(12) United States Patent
Adams et al.

(10) Patent No.: US 11,332,711 B1
(45) Date of Patent: May 17, 2022

(54) SPOROZOITE CRYOPRESERVATION COMPOSITIONS AND METHODS

(71) Applicant: UNIVERSITY OF SOUTH FLORIDA, Tampa, FL (US)

(72) Inventors: John H. Adams, Tampa, FL (US); Alison Elizabeth Roth, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 438 days.

(21) Appl. No.: 16/376,975

(22) Filed: Apr. 5, 2019

Related U.S. Application Data

(60) Provisional application No. 62/653,377, filed on Apr. 5, 2018.

(51) Int. Cl.
| | |
|---|---|
| *A61K 38/08* | (2019.01) |
| *C12N 5/07* | (2010.01) |
| *A01N 1/02* | (2006.01) |
| *C12N 5/00* | (2006.01) |

(52) U.S. Cl.
CPC ......... *C12N 5/0601* (2013.01); *A01N 1/0221* (2013.01); *C12N 5/0018* (2013.01)

(58) Field of Classification Search
CPC ................................................... C12N 5/0601
See application file for complete search history.

(56) References Cited

U.S. PATENT DOCUMENTS

| | | | |
|---|---|---|---|
| 8,043,625 | B2 | 10/2011 | Sim et al. |
| 2007/0169209 | A1 | 7/2007 | Hoffman et al. |
| 2016/0287688 | A1 | 10/2016 | Eappen et al. |

OTHER PUBLICATIONS

Singh et al., Parasitology International, 2016, 65:552-557.*
Bafort, WHO, 1967, pp. 1-9.*
Lupton et al., Parasitology International, 2015, 64:211-218.*
Patrapuvich et al., Viability and Infectivity of Cryopreserved Plasmodium Vivax Sporozoites, Southeast Asian Journal of Tropical Medicine and Public Health, 2016, 47(2):171-181.
Singh et al., Experimental Evaluation of Cryopreservative Solutions to Maintain In Vitro and In Vivo Infectivity of P. berghei Sporozoites, PLoS ONE, 2017, 12(5):e0177304, 14 pages.

* cited by examiner

*Primary Examiner* — Bin Shen

(57) ABSTRACT

Described herein are compositions and methods to cryopreserve sporozoites. In some aspects, the method can include the step of placing harvested salivary glands containing sporozoites into an insect-based medium.

17 Claims, 2 Drawing Sheets

SPOROZOITE CRYOPRESERVATION COMPOSITIONS AND METHODS

CROSS-REFERENCE TO RELATED APPLICATIONS

This application claims the benefit of and priority to U.S. Provisional Patent Application No. 62/653,377, filed on Apr. 5, 2018, entitled "SPOROZOITE CRYOPRESERVATION COMPOSITIONS AND METHODS," the contents of which is incorporated by reference herein in its entirety.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 2A) *Plasmodium* sporozoites in an insect-based media retain viability measured by percent gliding for a minimum of 4 hours (T4) whereas sporozoites in a human-based media are non-viable at T4. (FIG. 2B) *Plasmodium* sporozoites in an insect-based media infect PHH at a higher rate (greater than about 3-fold) compared to sporozoites in a human-based media.

BACKGROUND

Figure 1:
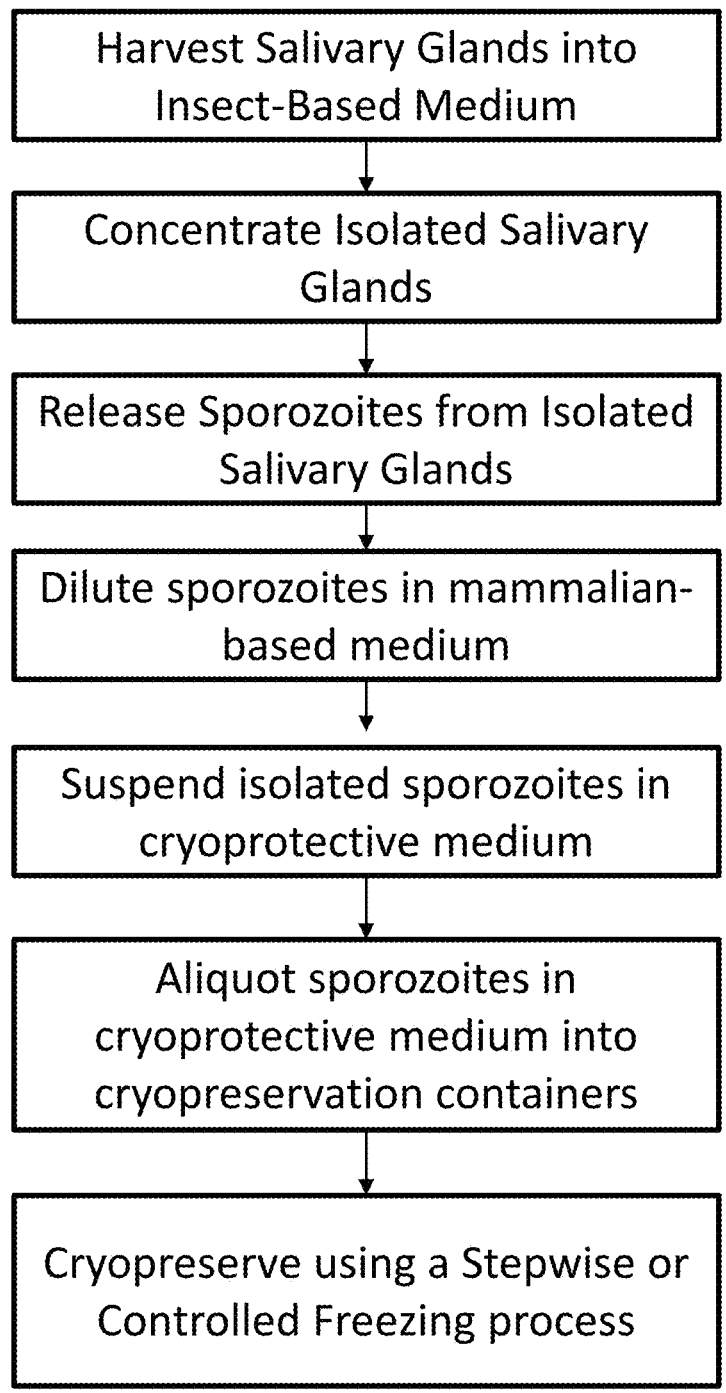
FIG. 1 shows a flow chart showing aspects of a method to cryopreserve sporozoites.

Malaria is still the most deadly parasitic disease of humans with most lethal cases associated with infection by *Plasmodium falciparum*. Plasmodia, the causative agents of malaria in many vertebrates, are transmitted mostly by *Anopheles* mosquitos. In mammals, *Anopheles* injects about 10 to 100 *Plasmodium* sporozoites into the skin, where the parasites migrate and enter the blood and/or lymph vessels. The sporozoites entering the blood can reach the liver, where they continue the infectious life cycle ultimately resulting in infection of the red blood cells and symptoms of the disease. Rising resistance against current anti-malarial agents necessitates research into new medications and vaccines. However, current drug and vaccine research and production is hindered by the current need to rely on fresh sporozoites. As such, there exists a need for improved compositions and techniques to allow for departure from reliance on fresh sporozoites.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10"

is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, organic chemistry, biochemistry, physiology, cell biology, parasitology, and the like, which are within the skill of the art. Such techniques are explained fully in the literature.

Definitions

As used herein, "concentrated" can refer to a molecule or population thereof, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "deoxyribonucleic acid (DNA)" and "ribonucleic acid (RNA)" can generally refer to any polyribonucleotide or polydeoxyribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "differentially expressed," can refer to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "expression" can refer to the process by which polynucleotides are transcribed into RNA transcripts. In the context of mRNA and other translated RNA species, "expression" also refers to the process or processes by which the transcribed RNA is subsequently translated into peptides, polypeptides, or proteins. In some instances, "expression" can also be a reflection of the stability of a given RNA. For example, when one measures RNA, depending on the method of detection and/or quantification of the RNA as well as other techniques used in conjunction with RNA detection and/or quantification, it can be that increased/decreased RNA transcript levels are the result of increased/decreased transcription and/or increased/decreased stability and/or degradation of the RNA transcript. One of ordinary skill in the art will appreciate these techniques and the relation "expression" in these various contexts to the underlying biological mechanisms.

As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, "overexpressed," "overexpression", or "up-regulated" can refer to an increased expression level of an RNA and/or protein product encoded by a gene as compared to the level of expression of the RNA or protein product in a normal or control cell.

As used herein, "separated" or "isolated" can refer to the state of being physically divided from the original source or population such that the separated compound, agent, particle, or molecule can no longer be considered part of the original source or population.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, "under expressed," "under expression," or "down regulated" can refer to decreased expression level of an RNA (coding or non-coding RNA) or protein product encoded by a gene as compared to the level of expression of the RNA or protein product in a normal or control cell.

Discussion

Malaria is still the most deadly parasitic disease of humans with most lethal cases associated with infection by *Plasmodium falciparum*. Plasmodia, the causative agents of malaria in many vertebrates, are transmitted mostly by *Anopheles* mosquitos. In mammals, *Anopheles* injects about 10 to 100 *Plasmodium* sporozoites into the skin, where the parasites migrate and enter the blood and/or lymph vessels. The sporozoites entering the blood can reach the liver, where they continue the infectious life cycle ultimately resulting in infection of the red blood cells and symptoms of the disease. Sporozoites of the malaria parasite *Plasmodium*, represent infective cells of a eukaryote parasite and are required for disease transmission between the arthropod vector to mammalian host. Therapeutic use and targeting of the sporozoite and subsequent formed liver stages are important to malaria eradication. Rising resistance against current anti-malarial agents necessitates research into new medications and vaccines.

However, current drug and vaccine research and production is hindered by the current need to rely on fresh sporozoites. Indeed, aseptic isolation of sporozoites has proven difficult and thus it is difficult to produce the quantities required for drug and vaccine studies. Furthermore, freshly isolated sporozoites are only viable for a few hours, thus creating a further functional limitation to their use in drug and vaccine development. As such, there exists a need for improved compositions and techniques to allow for departure from reliance on fresh sporozoites. Specifically, there is an immediate need for improved methods and techniques for the isolation, preparation, and/or storage of sporozoites.

With that said, described herein compositions and methods that can allow for simple and effective harvesting, processing, and/or preservation of sporozoites. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Cryopreservation of Sporozoites

Described herein are aspects of a method to cryopreserve sporozoites. FIG. 1 shows a flow-chart that can show aspects of a method to cryopreserve sporozoites. The time from harvesting the salivary glands, through processing, and to the cryopreservation step can be less than an hour. Generally, the methods to cryopreserve sporozoites can start with harvesting salivary glands from an infected mosquito and holding them in an insect-based salivary gland collection medium. The salivary glands can be harvested using any standard dissection technique. In some aspects, sterile or aseptic dissection and collection techniques can be used to harvest the salivary glands.

The insect-based salivary gland collection medium can be a serum-free insect-based salivary gland collection medium. The insect-based salivary gland collection medium can be can also contain sodium bicarbonate and/or sodium chloride and made isotonic to insect cells. The pH of the insect-based salivary gland collection medium can be about 7 (a neutral pH). The volume of insect-based salivary gland collection medium used can range from about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or about 99 µL to about 100 µL, including any range or value therein. The insect-based collection medium can be pre-chilled to about 4° C. and can be maintained at about 4° C. throughout the collection and isolation processes. Suitable insect-based salivary gland collection medium can be composed completely of or include one or more of the following media: Schneider's medium, Grace's medium, Leibowitz medium, Shield's medium, THM-FH medium, ExCell medium, IPL-41 medium, and TC-100 medium, without limitation. The use of an insect-based salivary gland collection media can up-regulate genes involved in gliding motility and/or human hepatocyte invasion, increase sporozoite viability, and/or infectivity.

Current methods for isolating and preserving sporozoites are based off of techniques for mammalian cell types as opposed to insect cell types. As shown in FIG. 1, in aspects of the method described herein, salivary glands are harvested and held in an insect-based collection medium. This is different than current methods that harvest the salivary glands and hold them in a mammalian-based medium at this point in the process.

Immediately following harvesting of the salivary glands, the salivary glands can be concentrated by centrifugation at about 16,000 RCF for about 3 minutes. Following centrifugation, the sporozoites can be released from the salivary glands using a suitable technique. In some aspects, the sporozoites can be released from the salivary glands by mechanical disruption using a suitable technique (e.g. by pestle and manual pipette manipulation). Sporozoites can then be quantified. The sporozoites can then be diluted to about $10^4$ cells/µL to about $10^7$ cells/µL (or any range or value therein) in a total volume of about 25 to 250 µL (or any other range or value therein) in a suitable mammalian-based medium. Suitable mammalian-based mediums can include, but is not limited to, RPMI, Modified Eagle Medium, Dulbecco's Modified Eagle Medium, Leibowitz medium, F12, and Complete InVitroGRO CP Medium. In some aspects, the mammalian-based medium is RPMI. The mammalian-based medium can be supplemented with serum (fetal bovine and/or human), bovine serum albumin, hypoxanthine, L-glutamine, HEPES, and any combination thereof. In some aspects, the mammalian-based medium is RPMI supplemented with hypoxanthine, L-glutamine, and HEPES.

Next, isolated sporozoites can be immediately suspended in a suitable cryoprotective medium. Suitable cryoprotective mediums can be, without limitation, CryoStor2, CryoStor5, CryoStor10, and combinations thereof. In some aspects, the cryoprotective medium is CryoStor2. The suitable cryoprotective medium can contain about 2-10% DMSO (dimethyl sulfoxide). The suitable cryoprotective medium can contain about 0-90% fetal bovine serum. The suspended sporozoites can then be dispensed into ultra-low temperature freezer-safe containers in aliquots each having a volume from 100 µL to 1 mL.

To cryopreserve the aliquots, a stepwise or controlled-rate freezing process can be used. In some aspects, a freezing rate of about −1° C./sec to about −25° C./min until a final temperature of about −80° C. For the stepwise method, dispensed sporozoites can be incubated for about 30 min at about 4° C. then transferred to about −80° C. for about 1 hour and up to 12 hours. After this incubation at −80° C. a final transfer to liquid nitrogen vapor phase can be conducted for prolonged storage. Per controlled-rate freezing process the following parameters can be followed with a seeding conducted mid-process (Table 2, event number 4) to induce controlled ice formation and minimize cell damage.

To thaw the cryopreserved sporozoites for use, the cryopreserved sporozoites can be thawed in to pre-warmed (about 37° C.) suitable mammalian-based medium. Suitable mammalian-based mediums for thawing include, but are not limited to, RPMI, Modified Eagle Medium, Dulbecco's Modified Eagle Medium, Leibowitz medium, F12, and Complete InVitroGRO CP Medium. The suitable mammalian-based medium can be supplemented with serum (fetal bovine or human), bovine serum albumin, hypoxanthine, L-glutamine, HEPES and any combination thereof. In some aspects, the suitable mammalian-based medium can be supplemented with serum (fetal bovine or human), bovine serum albumin, hypoxanthine, L-glutamine, and HEPES, which can be referred to as Complete CP Medium. In some aspects the mammalian-based medium is InVitroGRO Complete CP Medium. In some aspects, the thermostabilized cryopreserved vial of sporozoites can be removed from liquid nitrogen or other ultra-low temperature storage and carefully thawed at ambient room temperature or in a 37° C. water bath until almost completely thawed with ice entirely melted but no longer than it takes to completely thaw the cryostorage vial. Pre-warmed (about 37° C.) InVitroGRO Complete CP Medium (or other suitable mammalian-based medium) can be immediately added at volume ranges from about 0.1 to about 1 mL. In some aspects, the volume of the mammalian-based medium can be about 100 µL.

Performance or other characteristics of the sporozoites can be measured. Such characteristics can include, but are not limited to, RNA and/or protein expression, amount, or activity, sporozoite viability, sporozoite infectivity using assays, techniques, and methods generally known to the skilled artisan. Example bioassays can include, but are not limited to, motility assays and host cell infectivity assay. Suitable host cell infectivity assays include, but are not limited to, a primary human hepatocyte invasion assay for *Plasmodium* sporozoites.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Infected mosquito salivary glands were dissected using standard aseptic dissection techniques. A serum-free insect-based salivary gland collection/holding medium was prepared. The serum-free insect-based salivary gland collection/holding medium also contained no sodium bicarbonate and sodium chloride as detrimental to *Plasmodium* sporozoite The pH of the serum-free insect-based salivary gland collection medium was adjusted to about 7 (a neutral pH). Specifically, the serum-free insect-based salivary gland collection medium contained: Schneider's insect media (Table 1). Salivary glands during and after dissection and collection were maintained at about 4° C. The serum-free insect-based salivary gland collection medium was pre-chilled to about 4° C. prior to the addition of harvested salivary glands.

TABLE 1

Components of experimental mediums.

|  | RPMI 1640 (mg/L) | Schneider's (mg/L) |
| --- | --- | --- |
| Inorganic Salts | | |
| Potassium chloride (KCl) | 400 | 1,600 |
| Sodium bicarbonate (NaHCO$_3$) | — | — |
| Sodium chloride (NaCl) | 6,000 | 2,100 |
| Sodium phosphate dibasic (Na$_2$HPO$_4$) (anhyd) | 800 | 700 |
| Calcium nitrate (Ca(NO$_3$)$_2$ 4H$_2$0) | 100 | |
| Magnesium sulfate (MgSO$_4$) (anhyd) | 48.84 | 1,807.221 |
| Other Components | | |
| D(+)-Glucose | 2,000 | 2,000 |
| D(+)-Trehalose | — | 2,000 |
| Fumaric acid | — | 60 |
| Succinic acid | — | 60 |
| Yeast extract | — | 2,000 |
| L-(−)-Malic acid | — | 600 |
| α-Ketoglutaric acid | — | 350 |
| Glutathione (reduced) | 1 | — |
| Phenol red | 5.3 | — |
| Hypoxanthine | 50 | — |
| HEPES | 10,400 | — |
| Vitamins | | |
| D-biotin | 0.2 | — |
| Choline chloride | 3 | — |
| Folic acid | 1 | — |
| Niacinamide | 1 | — |
| p-aminobenzoic acid | 1 | — |
| D-pantothenic acid ½ Ca | 0.25 | — |
| Pyridoxine hydrochloride (HCl) | 1 | — |
| Riboflavin | 0.2 | — |
| Thiamine hydrochloride | 1 | — |
| Vitamin B12 | 0.005 | — |
| myo-inositol | 35 | — |
| Amino Acids | | |
| Glycine | 10 | 250 |
| L-Arginine | 200 | 600 |
| L-Asparagine | 50 | — |
| L-Aspartic acid | 20 | 400 |
| L-Cystine 2HCl | 65 | 26.732 |
| L-Cysteine | — | 60 |
| L-Glutamic acid | 20 | 800 |
| L-Glutamine | 300 | 1,800 |
| L-Histidine | 15 | 400 |
| L-Hydroxyproline | 20 | — |
| L-Isoleucine | 50 | 150 |
| L-Leucine | 50 | 150 |
| L-Lysine hydrochloride | 40 | — |
| L-Lysine | — | 1,650 |

TABLE 1-continued

Components of experimental mediums.

| | RPMI 1640 (mg/L) | Schneider's (mg/L) |
|---|---|---|
| L-Methionine | 15 | 150 |
| L-Phenylalanine | 15 | — |
| L-Proline | 20 | 1,700 |
| L-Serine | 30 | 250 |
| L-Threonine | 20 | 350 |
| L-Tryptophan | 5 | 100 |
| L-Tyrosine disodium salt dihydrate | 28.83 | 72.02 |
| L-Valine | 20 | 300 |
| β-Alanine | — | 500 |
| (anhyd) means anhydrogenous | — | — |

After initial isolation, a gene expression analysis was performed. The results are demonstrated in Table 2. As shown in Table 2, initial isolation of sporozoites in an insect-based media can preserve the sporozoite in a quiescent state with up-regulation of genes necessary for gliding motility and human hepatocyte invasion.

Immediately following harvesting of the salivary glands, the salivary glands were concentrated by centrifugation at about 16,000 RCF for about 3 minutes. Following centrifugation, the salivary glands were mechanically disrupted (e.g. by pestle and manual pipette manipulation), which released the sporozoites from the salivary glands. Sporozoites were then quantified, diluted to about $1 \times 10^4$ cells/μL and $4 \times 10^4$ cells/μL in a total volume of 25 μL in a mammalian-based medium. In this Example, the mammalian-based medium was RPMI supplemented with hypoxanthine, L-glutamine, and HEPES (Table 1).

Next, isolated sporozoites were immediately suspended in a cryoprotective medium (CryoStor2) that contained about 2% DMSO. The suspended sporozoites were dispensed into ultra-low temperature freezer-safe containers in a volume of about 100 μL.

The dispensed sporozoites were then cryopreserved using a stepwise freezing process. For the stepwise freezing process, the dispensed sporozoites were then cryopreserved by the following protocol: sporozoites were incubated for about 30 min at about 4° C. then transferred to about −80° C. for

TABLE 2

List of known top 30 Plasmodium vivax sporozoite viability genes

| Gene ID | Product description | Gene symbol | p-value |
|---|---|---|---|
| PVP01_1105500 | nucleoside diphosphate kinase, putative | NDK | 3.29564E−06 |
| PVP01_1132600 | TRAP-like protein putative | TLP | 1.38308E−09 |
| PVP01_0613800 | merozoite TRAP-like protein, putative | MTRAP | 1.72207E−08 |
| PVP01_1226800 | nicotinamide/nicotinic acid mononucleotide adenylyltransferase, putative | NMNAT | 0.009330955 |
| PVP01_1124400 | sphingomyelin synthase 2, putative | SMS2 | 0.016032266 |
| PVP01_0607900 | phospholipid scramblase, putative | null | 0.000333428 |
| PVP01_1258000 | gamete egress and sporozoite traversal protein, putative | GEST | 0.014301705 |
| PVP01_1249700 | thioredoxin 1, putative | TRX1 | 1.77136E−05 |
| PVP01_0920900 | CorA-like Mg2+ transporter protein, putative | MIT1 | 1.1193E−08 |
| PVP0_1245400 | phosphatidylinositol-4-phosphate 5-kinase, putative | PIP5K | 1.2595E−07 |
| PVP01_0615300 | claudin-like apicomplexan microneme protein, putative | CLAMP | 1.11382E−08 |
| PVP01_1224800 | apicoplast calcium binding protein 1, putative | ACBP1 | 2.30496E−08 |
| PVP01_1436800 | thrombospondin-related apical membrane protein, putative | TRAMP | 0.001004392 |
| PVP01_1321700 | CorA-like Mg2+ transporter protein, putative | MIT3 | 0.000347254 |
| PVP01_1212700 | iron regulatory protein, putative | IRP | 1.52706E−08 |
| PVP01_0114800 | serine/threonine protein kinase, FIKK family | FIKK | 3.22841E−05 |
| PVP01_0943700 | alpha/beta hydrolase, putative | alpha/beta hydrolase | 1.11071E−05 |
| PVP01_0928000 | tRNA (guanine-N(7)-)-methyltransferase, putative | tRNA (guanine-N(7)-)-methyltransferase | 1.93339E−05 |
| PVP01_0728800 | merozoite surface protein 1 paralog | MSP1P | 0.000976792 |
| PVP01_1223600 | protein kinase, putative | PK | 2.44094E−08 |
| PVP01_0313300 | calcium-dependent protein kinase 4, putative | CDPK4 | 0.001403133 |
| PVP01_1141700 | uroporphyrinogen III decarboxylase, putative | UROD | 1.42624E−09 |
| PVP01_1456100 | COPI associated protein, putative | COPI | 7.03881E−10 |
| PVP01_1464100 | DNA replication origin binding protein, putative | DIA2 | 0.000731438 |
| PVP01_0112200 | plasmepsin X, putative | PMX | 3.37727E−11 |
| PVP01_1322600 | phosphoenolpyruvate carboxylase, putative | PEPC | 0.017136065 |
| PVP01_0303900 | 6-cysteine protein, putative, pseudogene | 6-cys | 3.81458E−06 |
| PVP01_0921000 | alpha/beta hydrolase fold domain containing protein, putative | alpha/beta hydrolase | 1.41824E−07 |
| PVP01_0519100 | vacuolar protein sorting-associated protein 2, putative | VPS2 | 0.00022923 |
| PVP01_0906300 | centrin-4, putative | CEN4 | 2.86033E−07 |

1 hour, then finally transferred to liquid nitrogen vapor phase for prolonged storage. For the controlled-rate freezing process, a freezing rate of about −1° C. per second to about −25° C. per minute until a final temperature of about −80 to about −90° C. is reached with transfer to liquid nitrogen vapor phase for prolonged storage. Table 3 shows the parameters for the controlled rate freezing process that was employed. Seeding mid-process was conducted (Table 3, event number 4) to induced controlled ice formation and minimize cell damaged. The total time from initial dissection and harvesting of the salivary glands to cryopreservation was not greater than 1 hour.

TABLE 3

Parameters for controlled rate freezing.

| Event number | Rate of temperature change | Event |
|---|---|---|
| 1 | Cool chamber and sample to 4° C. | Hold until manually advanced |
| 2 | −1° C./minute | −4° C. sample temperature |
| 3 | −25° C./minute | −40° C. chamber temperature |
| 4 | +15° C./minute | −12° C. chamber temperature |
| 5 | −1° C./minute | −40° C. chamber temperature |
| 6 | −10° C./minute | Hold at −90° C. chamber temperature |
| 7 | — | End |

For thawing, the cryopreserved sporozoites were thawed into prewarmed (37° C.) mammalian-based medium (InVitroGRO CP medium) supplemented with serum, bovine serum albumin, hypoxanthine, L-glutamine, and HEPES (also referred to as InVitroGRP CP complete medium). Briefly, the thermostabilized cryopreserved vials of sporozoites were removed from liquid nitrogen or other ultra-low temperature storage and carefully thawed at ambient room temperature or in a 37° C. water bath until almost completely thawed with ice entirely melted but no longer than it takes to completely thaw the cryostorage vial. Pre-warmed InVitroGRO Complete CP Medium was immediately added at volumes ranging from about 0.1 to about 1 mL to reach a final dilution of about $1\times10^3$ sporozoites/μL.

Figure 2A:
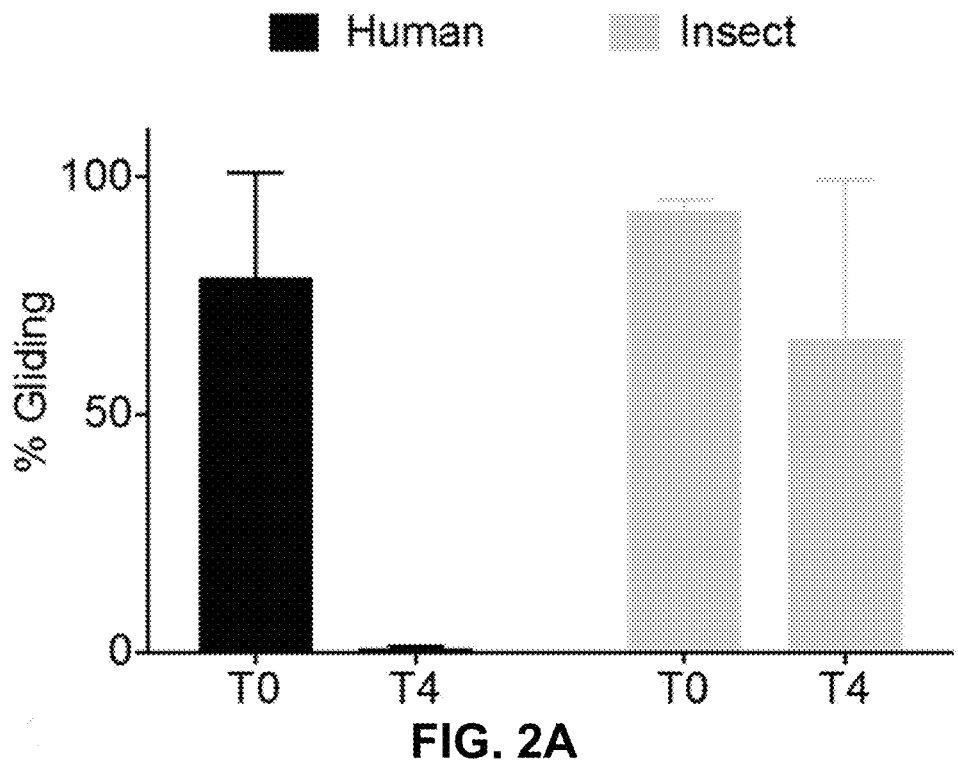
FIGS. 2A and 2B show graphs that can demonstrate a comparison of *Plasmodium* sporozoite viability and primary human hepatocyte (PHH) invasion between human-like microenvironment and insect-like microenvironment.
Figure 2B:
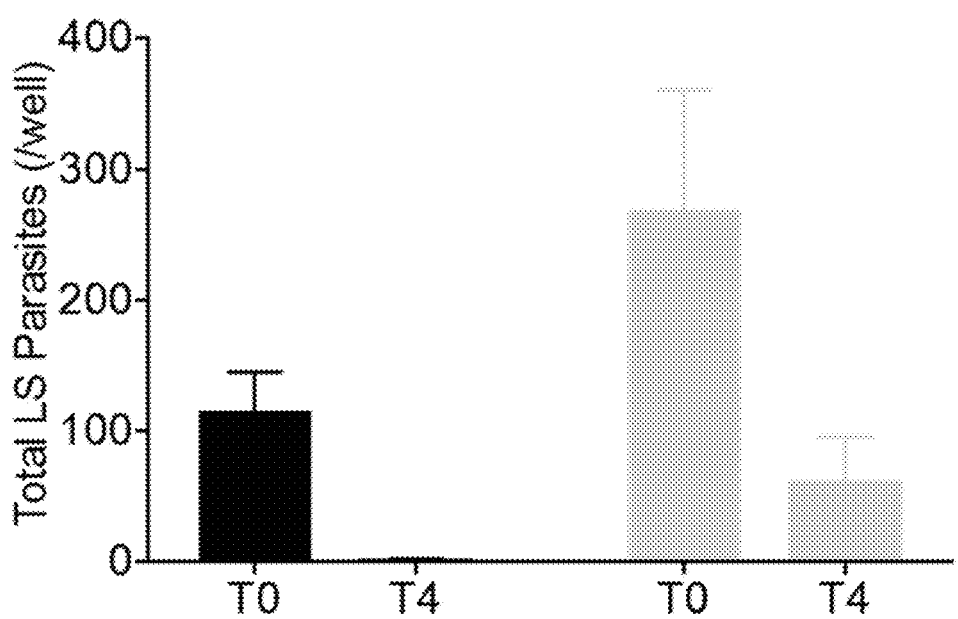

The percent viability and percent infection of the cryopreserved and thawed sporozoites was determined using a standard bioassay, such as a motility assay and host cell infectivity assay. FIGS. 2A and 2B show graphs demonstrating the results from a viability assay (FIG. 2A) and an infectivity assay (FIG. 2B). The viability assay was a gliding assay and the infectivity assay was a primary human hepatocyte invasion assay for *Plasmodium* sporozoites. As can be demonstrated by the results shown in FIGS. 2A and 2B, the use of an insect based medium (as opposed to a mammalian-based medium) during the initial collection of the salivary glands increased the viability of the sporozoites and their infectiveness as demonstrated by the primary human hepatocyte invasion assay. This is in addition to the observation that using an insect-based media at the initial collection stage also corresponded to an up-regulation of genes necessary for gliding motility and human hepatocyte invasion (Table 2).

We claim:

1. A method to cryopreserve sporozoites, the method comprising:
    a) placing harvested salivary glands containing sporozoites into an insect-based medium, the insect-based medium comprising Schneider's insect media as shown in Table 1;
    b) concentrating the salivary glands;
    c) releasing sporozoites from the salivary glands;
    d) diluting sporozoites in a mammalian based medium, the mammalian-based medium comprising RPMI1640 as shown in Table 1;
    e) suspending diluted sporozoites in a cryoprotective medium;
    f) aliquoting the sporozoites in the cryoprotective medium into cryopreservation containers; and
    g) cryopreserving the aliquots using a stepwise or controlled freezing process.

2. The method of claim 1, wherein the harvested salivary glands are from a mosquito.

3. The method of claim 1, wherein the sporozoites are of the genus *Plasmodium*.

4. The method of claim 1, wherein the time from placing the harvested salivary glands containing sporozoites into an insect-based medium to starting the step of cryopreserving the aliquots occurs in one hour or less.

5. The method of claim 1, wherein the entire method is carried out in 1 hour or less.

6. The method of claim 1, wherein the insect-based medium is serum free.

7. The method of claim 1, wherein the insect-based medium is isotonic to insect cells.

8. The method of claim 1, wherein the insect-based medium is about pH 7.

9. The method of claim 1, wherein the insect-based medium is at a temperature of about 4° C.

10. The method of claim 1, wherein the salivary glands are concentrated via centrifugation during the step of concentrating.

11. The method of claim 1, wherein the sporozoites are released via mechanical disruption of the salivary glands during the step of releasing.

12. The method of claim 1, wherein the sporozoites are diluted to about $10^4$ cells/μL to about $10^7$ cells/μL during the step of diluting.

13. The method of claim 1, wherein the sporozoites are diluted in a volume ranging from about 25 μL to about 250 μL during the step of diluting.

14. The method of claim 1, wherein the mammalian based medium is supplemented with serum, bovine serum album, hypoxanthine, L-glutamine, HEPES, or any combination thereof.

15. The method of claim 1, wherein the cryoprotective medium comprises about 2 to about 10% dimethyl sulfoxide.

16. The method of claim 1, wherein the cryoprotective medium comprises about 0-90% fetal bovine serum.

17. The method of claim 1, wherein the aliquots formed during the step of aliquoting each have a volume ranging from about 100 μL to 1 ml.

* * * * *